(12) United States Patent
Zhou et al.

(10) Patent No.: US 9,943,560 B2
(45) Date of Patent: Apr. 17, 2018

(54) MEDICAL COMPOSITIONS CONTAINING LIQUORICE EXTRACTS WITH SYNERGISTIC EFFECT

(76) Inventors: James Zhou, Beijing (CN); Dong Chen, Beijing (CN)

( * ) Notice: Subject to any disclaimer, the term of this patent is extended or adjusted under 35 U.S.C. 154(b) by 1374 days.

(21) Appl. No.: 13/577,276

(22) PCT Filed: Jan. 26, 2011

(86) PCT No.: PCT/CN2011/070614
§ 371 (c)(1),
(2), (4) Date: Feb. 5, 2013

(87) PCT Pub. No.: WO2011/095095
PCT Pub. Date: Aug. 11, 2011

(65) Prior Publication Data
US 2013/0149393 A1 Jun. 13, 2013

(30) Foreign Application Priority Data
Feb. 6, 2010 (CN) .......................... 2010 1 0107982

(51) Int. Cl.
| | | |
|---|---|---|
| A61K 36/00 | (2006.01) |
| A61K 36/484 | (2006.01) |
| A61K 31/404 | (2006.01) |
| A61K 31/513 | (2006.01) |
| A61K 33/24 | (2006.01) |
| A61K 36/815 | (2006.01) |
| A61K 45/06 | (2006.01) |
| A61K 31/12 | (2006.01) |

(52) U.S. Cl.
CPC ............ *A61K 36/484* (2013.01); *A61K 31/12* (2013.01); *A61K 31/404* (2013.01); *A61K 31/513* (2013.01); *A61K 33/24* (2013.01); *A61K 36/815* (2013.01); *A61K 45/06* (2013.01)

(58) Field of Classification Search
CPC ...................................................... A61K 36/00
See application file for complete search history.

(56) References Cited

U.S. PATENT DOCUMENTS

| | | | | |
|---|---|---|---|---|
| 6,103,240 A * | 8/2000 | Zhou | ...................... | A01N 65/00 424/757 |
| 7,166,311 B2 | 1/2007 | Ikehara et al. | | |
| 2007/0098761 A1 | 5/2007 | Arai et al. | | |
| 2009/0226545 A1* | 9/2009 | Blotsky | ................. | A23L 1/2366 424/725 |

FOREIGN PATENT DOCUMENTS

| | | |
|---|---|---|
| CN | 1179945 | 4/1998 |
| CN | 1813870 | 8/2006 |
| CN | 101181548 | 5/2008 |

OTHER PUBLICATIONS

Fukai et al, Antimicrobial activity of licorice flavonoids against methicillin-resistant *Staphylococcus aureus*. Fitoterapia (2002), vol. 73, No. 6, pp. 536-539.*
Gao et al, Study on the antibacterial activity of Ch. Wolfberry Polysaccharide. Shipin Keji (2007), (10), 100-102.*
International search report dated Apr. 28, 2011.

* cited by examiner

*Primary Examiner* — Qiuwen Mi
(74) *Attorney, Agent, or Firm* — Bachman & LaPointe, PC

(57) ABSTRACT

The invention provides drug compositions with synergistic effects, which includes alcohol-soluble and water-insoluble liquorices extracts and at least one kind of anti-tumor or glucose-and-lipid-lowering drug/eatable substance, and can be used to treat tumor or lower blood glucose and lipid. Besides, the invention also provides pharmaceutical preparation, pharmaceutical application, therapeutic and preparation methods, etc. related to this drug compositon.

14 Claims, No Drawings

MEDICAL COMPOSITIONS CONTAINING LIQUORICE EXTRACTS WITH SYNERGISTIC EFFECT

TECHNOLOGY FIELD

This invention belongs to the medicine technical field. Specifically, this invention involves drug compound with synergistic effect, including alcohol-soluble and water-insoluble liquorices extracts, and at least one kind of anti-tumor or glucose-and-lipid-lowering drug, and can be used to treat tumor or lower blood glucose and lipid. In addition, this invention involves pharmaceutical preparation, pharmaceutical application, therapeutic and preparation methods, etc. related to this drug compound.

TECHNOLOGY BACKGROUND

In China, the drug utilization of traditional Chinese medicine plants has a long history, and the Chinese medicines extracted from Chinese medicine plants by decoction of them in water, wine and so on are extensively used and have saved a lot of lives in history. Modern research shows that many a traditional Chinese medicine plant takes effect through its flavonoid compounds, separate out single ingredient to prepare modern drugs, for example, Chinese patent application CN1113909A, CN1371372A and so on. However, due to numerous ingredients of traditional Chinese medicine, medicinal mechanism is hard to reveal completely. In particular, synergistic mechanisms between different ingredients or between their ingredients and other drugs are too complicated for modern medicine to reveal, even the more researched *Radix Glycyrrhizae* (also called lantern, matsumura leafflower herb, liquorice, Lu grass, powder grass, canton hedyotis herb, sacharum spontaneum, polypogon fugax), the ingredients in extracts of which include glycyrrhizic acid, licoflavone, liquirit igenin, liquiritin, glabridin, Chalcone and so on. The therapeutic effectiveness among ingredients, therapeutic effectiveness and therapeutic effectiveness stability between their ingredients and other drugs are seldom studied. Therefore, the drugs extracted and prepared with traditional Chinese medicine plants are generally only utilized in pharmaceutical products of China, India, Japan and other countries.

Chinese medicine prescription and traditional Chinese medicine preparation are commonly used for therapy in Chinese medicine, but the therapeutic effectiveness is not stable. The reason lies in the difficulty in getting knowledge of the correlation of Chinese medicine ingredients in Chinese medicine prescription and medicine preparation with indications. Moreover, there is a significant link between Chinese medicine ingredients and extraction method, extracting materials as well as material standards, which means a slightest difference in initial materials would lead to totally different drug efficacy. Therefore, though the concept that traditional Chinese medicine is natural has been widely acknowledged among patients in the United States and Europe, and they are utilized for therapy and health care, the stability of therapeutic effectiveness restrict its promotion and application in these areas.

After long-term research, the inventor surprisingly thought out an all new idea of extracting liquorices extracts with simplified preparation process, which reserves one or various effective ingredients. Even though the application of different liquorices materials results in great difference in effective ingredients of extracts (e.g. extracts may not contain Chalcone A or contain the preferred Chalcone A), they are all therapeutically effective in anti-tumor or lowering glucose and lipid, especially when they are combined with other anti-tumor or glucose-and-lipid-lowering drug, the synergistic effect can be enhanced, accordingly to reduce the dose of active pharmaceutical ingredient (especially the ingredient with strong side effect) and greatly improve the safety of medication use.

INVENTION SUMMARY

This invention aims to provide alcohol-soluble and water-insoluble liquorices extracts. It can be utilized alone or combined with anti-tumor or glucose-and-lipid-lowering drugs. In addition, this invention also provides relevant drug compounds, pharmaceutical preparation, application and method and so on. In the first aspect, this invention provides drug composition with synergistic effect, including alcohol-soluble and water-insoluble liquorices extracts, and at least one kind of anti-tumor or glucose-and-lipid-lowering drug. Preferably, alcohol-soluble and water-insoluble liquorices extracts, and at least one kind of anti-tumor or glucose-and-lipid-lowering drug are all active pharmaceutical ingredients. More preferably, it is composed of alcohol-soluble and water-insoluble liquorices extracts and a kind of anti-tumor or glucose-and-lipid-lowering drug.

In preferred drug composition of the first aspect of this invention, liquorices are *Radix glycyrrhiza* including *Glycyrrhiza uralensis* or *Glycyrrhiza inflata* or their mixture. The preferred liquorices is the mixture of *Glycyrrhiza uralensis* and *glycyrrhiza inflata,* for example, the preferred *glycyrrhiza inflata* content shall be no less than 5%, and the preferred *Glycyrrhiza uralensis* content shall be no less than 5%. Therefore, in preferred drug compound of the first aspect of this invention, liquorices extracts is the extracts of *Radix glycyrrhiza* and that of *glycyrrhiza inflata* or their mixture. The preferred liquorices extracts is the mixture of *Glycyrrhiza uralensis* and *glycyrrhiza inflata* extracts, for example, the preferred *glycyrrhiza inflata* content shall be no less than 5%, the Chalcone A content shall be no less than 5%. Liquorices extracts compound can be extracted for preparation after mixing different liquorices, or be mixed for preparation after extracting liquorices extracts.

In the preferred first aspect drug compositon of this invention, the preparation of alcohol-soluble and water-insoluble liquorices extracts include the following steps:

(1) Reserve the solid part after the extraction of liquorices by water.

(2) Reserve and dry the liquid part, after extracting the solid part by extraction steps (1) with a high concentration alcohol (concentrations is higher than 85% (V/V), the preferred is higher than 90% (V/V), more preferred is higher than 93% ((V/V)), such as 95% (V/V)) . The preferring way also includes the steps for further extraction of Chalcone A. In this way, alcohol-soluble and water-insoluble liquorices extracts is Chalcone A extracted from liquorices.

In preferred drug compound of the first aspect of this invention, *glycyrrhiza* flavonoids content in alcohol-soluble and water-insoluble liquorices extracts shall exceed 15%, e.g. 20%, which may contain Chalcone A or not; but the preferred one contains Chalcone A, or Chalcone A content in alcohol-soluble and water-insoluble liquorices extracts shall exceed 5%, e.g. 15%, In preferred drug composition of the first aspect of this invention, anti-tumor or glucose-and-lipid-lowering drugs are effective in anti-tumor or glucose and lipid-decreasing, or another invented alcohol-soluble and water-insoluble liquorices extracts, or drugs exactly effective at current. The preferred are one or more in 5- fluorouracil, indole-3-carbinol (I3C) or 3,3'-diindolymethane (DIM) or its other derivatives (e.g. indole tris-methanol), cis-platinum complexes and Chinese wolfberry.

In the second aspect, this invention provides pharmaceutical preparation of anti-tumor or glucose and lipid-decreasing, including the drug compound of the first aspect of this invention and acceptable auxiliary adjuvant in pharmacy. The dose of preferred drug compound of the first aspect of this invention is safe and effective.

The alcohol-soluble and water-insoluble liquorices extracts in this invention can take synergistic effect with various commonly-used anti-tumor or glucose-and-lipid-lowering drugs. Therefore, the preferred dose of anti-tumor or glucose-and-lipid-lowering drug contained in composition of the first aspect of this invention shall be less than the dose of anti-tumor or glucose-and-lipid-lowering drug by using them alone to achieve the same effect.

In the third aspect, this invention provides alcohol-soluble and water-insoluble liquorices extracts and at least one kind (the preferred one) of anti-tumor or glucose-and-lipid-lowering drug as all active pharmaceutical ingredients for application into preparation of anti-tumor or glucose-and-lipid-lowering drugs. This enhances the effectiveness and safety of drugs.

In preferred application of the third aspect of this invention, the described alcohol-soluble and water-insoluble liquorices extracts is the same as preferred in the first aspect of this invention.

In preferred application of the third aspect of this invention, the described anti-tumor or glucose-and-lipid-lowering drug is the same as preferred in the first aspect of this invention.

In the fourth aspect, this invention provides the method to treat tumor or decrease glucose and lipid, including giving effective dose of alcohol-soluble and water-insoluble liquorices extracts and effective dose of at least one kind (the preferred one) of anti-tumor or glucose-and-lipid-lowering drug to individuals.

In preferred method of the fourth aspect of this invention, the described alcohol-soluble and water-insoluble liquorices extracts is the same as preferred in the first aspect of this invention.

In preferred method of the fourth aspect of this invention, the described anti-tumor or glucose-and-lipid-lowering drug is the same as preferred in the first aspect of this invention.

In preferred method of the fourth aspect of this invention, the dosage is the same as preferred in the third aspect of this invention. In the fifth aspect, this invention provides the preparation method of alcohol-soluble and water-insoluble liquorices extracts, including:

(1) Reserve the solid part after the extraction of liquorices by water;
(2) Reserve and dry the liquid part, after extracting the solid part by extraction steps (1) with a high concentration alcohol (concentrations is higher than 85% (V/V), the preferred is higher than 90% (V/V), more preferred is higher than 93% ((V/V)), such as 95% (V/V)).
(3) Further to extract Chalcone A optionally, such as to extract Chalcone A by high speed countercurrent chromatography.

The preferred above methods are made up of the following steps:
(1) Reserve the solid part after the extraction of liquorices by water;
(2) Reserve and dry the liquid part, after extracting the solid part by extraction steps (1) with a high concentration alcohol (concentrations is higher than 85% (V/V), the preferred is higher than 90% (V/V), more preferred is higher than 93% ((V/V)), such as 95% (V/V)).
(3) Further to extract Chalcone A optionally, such as to extract Chalcone A by high speed countercurrent chromatography.

INVENTION DETAILS

This invention provides alcohol-soluble and water-insoluble liquorices extracts which can be utilized alone or combined with anti-tumor or glucose-and-lipid-lowering drug. The preparation methods of liquorices extracts includes the following steps:
(1) Reserve the solid part after the extraction of liquorices by water;
(2) Reserve and dry the liquid part, after extracting the solid part by extraction steps (1) with a high concentration alcohol (concentrations is higher than 85% (V/V), the preferred is higher than 90% (V/V), more preferred is higher than 93% ((V/V)), such as 95% (V/V)). The preferred way also includes the steps for further extraction of Chalcone A.

Among them, the means of reserving solid and liquid part is known to all, such as filtering and other solid-liquid separation methods. If the solid parts are required to be reserved, drying can be performed for further separating the remained liquid on the solid part.

Alcohol can be methyl alcohol, ethyl alcohol and others, but the most preferred one is ethyl alcohol, which further ensures the safety of products.

Among them, water extraction steps can be repeated many times, like 1-5 times; alcohol extraction steps can also be repeated many times, like 1-5 times, which can enhance alcohol solubility and water insolubility of liquorices extracts and improve its yield coefficient.

The preferred above methods include:
Crush the whole plants of liquorices and submerge it in 65-95° C. water for bathing about 1-15 hours; and then filter and reserve liquorices slag solid, dry it with temperature at 20-65° C. for 1-48 hours after being washed by water; inject 95% (V/V) ethanol into the dried liquorices slag solid, heat reflux (such as, 65-95° C.) for 0.5-8 hours, then filter out liquid, dry and remove liquid to obtain liquorices extracts.

The preferred above methods also include Chalcone A extraction steps, such as liquorices Chalcone A can be separated by high-speed countercurrent Chromatography (HSCCC) reported in Qiao-E. and Wang etc. (Journal of Chromatography A, 1048 (2004) 51-57), and the utilized solvent system is: n-hexane-chloroform-methanol-water.

In specific implementation modes, the method is applicable to both *Glycyrrhiza uralensis* and *glycyrrhiza inflata*. The alcohol-soluble and water-insoluble liquorices extracts of this invention may or may not contain Chalcone A, and the preferred one contains Chalcone A. In specific implementation methods of the invention, alcohol-soluble and water-insoluble liquorices extracts of this invention can take synergistic effect when combined with anti-tumor or glucose-and-lipid-lowering drugs. The liquorices flavonoids content in preferred alcohol-soluble and water-insoluble of liquorices extracts of this invention shall exceed 15%, such as 20%, which may or may not contain Chalcone A; Or, the Chalcone A content in alcohol-soluble and water-insoluble liquorices extracts shall exceed 5%, the preferred one shall exceed 10%, such as 15%. This can further stabilize drug efficacy as quality index.

The alcohol-soluble and water-insoluble of liquorices extracts in this invention can be used for medicinal purposes, such as anti-cancer, reducing blood lipid, or lowering blood glucose, etc. In this text, the term "Drug" includes not only drugs in terms of conventional understanding in this field, but also health products and foods with medicinal effect.

The alcohol-soluble and water-insoluble liquorices extracts in this invention can be mixed with pharmaceutically acceptable adjuvant to make pharmaceutical preparations. In this article, the term "pharmaceutically acceptable adjuvant" includes pharmaceutically acceptable carrier, excipient and diluent, etc. the active ingredients of which are compatible. It is well known among common technical personnel in this field to make pharmaceutical preparations with pharmaceutically acceptable adjuvant. The pharmaceutical preparations of the invention include one or more pharmaceutical compounds described in the first aspect of this invention as active ingredients, and combine the pharmaceutical compound with pharmaceutically acceptable adjuvant (such as the carrier, excipient and diluent, etc which is well known among common technical personnel in this field) to make a variety of preparations, the preferred of which are solid preparations and liquid preparations. The preparations of this invention can take the form of unit dosage such as tablets, pills, capsules (including sustained release or delayed release form), powders, suspensions, granules, tinctures, syrups, emulsions adjuvant, suspensions, injections, etc. and a variety of sustained-release dosage forms, thus to suit all kinds of medicine intake forms, such as oral, parenteral injection, mucous membrane, muscle, intravenous, subcutaneous, intraocular, intradermal, or skin penetration, etc. among which, the carrier, excipient and diluent are all pharmaceutically acceptable and compatible with active ingredients. Particularly, because the liquorices extracts of this invention are poor in alcohol-solubility and water-insolubility and are difficult to disperse when dried, therefore, the preferred may include the dispersant added in the making process of preparations such as nanometer dispersing adjuvant such as starch nanometer, nanometer-dextrin, nanometer-$SiO_2$, nanometer $CaCO_3$, nanometer $TiO_2$, nanometer zinc oxide, nanometer-indium, nanometer silver, nanometer aluminum hydroxide, nanometer iron oxide, nanometer ferric chloride, nanometer carbon, nanometer-selenium, nanometer-aluminum oxide, nanometer-magnesium oxide. And it is also preferred to make preparation particles by dispersing with physical methods (such as mechanical crushing) in the process of preparation making. Other suitable adjuvant includes poly ethylene glycol and poly-dimensional ketones water-soluble carriers, such as PEG2000-20000 or PVP K15-K90 or PVA or PVP-PVA or CPD and so on. Interstitial solid solution can be formed by the joint effort of such adjuvant and the active ingredients in the pharmaceutical compounds of the invention to further improve the drug dissolution rate and bioavailability.

The invention provides alcohol-soluble and water-insoluble liquorices extracts and at least one kind of (the preferred one) anti-tumor or glucose-and-lipid-lowering drug combination working as the active ingredients of all drugs for preparing anti-tumor or glucose-and-lipid-lowering drugs. The term "combination" indicates that alcohol-soluble and water-insoluble liquorices extracts and the anti-tumor or glucose-and-lipid-lowering drugs can be formulated in the same medicine formulation, and they can also be formulated in different ones, but different medicine formulation shall be included in the same drug through combined package and be used at the same time, in sequence or in turn, for example, the pharmaceutical dosage of alcohol-soluble and water-insoluble liquorices extracts can be oral preparation, and that of the anti-tumor or glucose-and-lipid-lowering medicine (For example, 5-fluorouracil) can be injection formulation, and these two pharmaceutical preparations will be used in combination form within the same anti-tumor or glucose- and-lipid-lowering drug package.

In order to reflect the advantage of synergistic effects, the preferred anti-tumor or glucose-and-lipid-lowering drugs used in combination with alcohol-soluble and water-insoluble liquorices extracts are medicines with toxic side effect itself or relatively weak efficacy and even those prone to produce medicine resistance. In the specific implementations of this invention, anti-tumor or glucose-and-lipid-lowering drugs can be 5-fluorouracil, indole-3-carbinol (I3C) or 3,3'-diindolymethane (DIM) or its other derivatives (e.g. indole tris-methanol), cis-platinum and/or wolfberry. 5-fluorouracil and cis-platinum will produce strong side effects when used alone, and they often develop medicine resistance in clinical practice; indole-3-carbinol (I3C) or 3,3'-diindolymethane (DIM) or its other derivatives (e.g. indole tris-methanol), has some anti-cancer effect, but it would be clinically effective only when used in large dosage which may cause side effects after a long period of time. The wolfberry is usually considered as a traditional Chinese medicine working as both food and medicine, and it is difficult to achieve satisfying effect on glucose lowering, lipid lowering and anti-cancer with common dosage.

The invention in this text provides anti-tumor or glucose-and-lipid-lowering methods which include giving effective dosage of alcohol-soluble and water-insoluble liquorices extracts and at least one kind (the preferred one) of anti-tumor or glucose-and-lipid-lowering drug of effective dosage to individuals. In this text, the individual refers to mammals needing treatment, and the preferred individual is human. In the specific implementations of this invention, the tumor is chosen from colon cancer, cervical endometrial cancer, breast cancer, prostate cancer and gastric cancer. The administering dose (effective dosage) and form is generally determined by physician in accordance with the patient's specific conditions (such as age, weight, gender, disease duration, physical condition, etc.). Generally speaking, the administration dose is 1~1000 mg/kg calculated by alcohol-soluble and water-insoluble liquorices extracts contained in the pharmaceutical compounds of this invention, and the preferred choice is 10~100 mg/kg according to patient weight. It must be specially pointed out that although the specific implementation of this invention gives a certain dose, the dose covered by this invention is not limited by it, the administration dose will change along with that of the specific conditions of patients, and selecting appropriate amount is within the ability of clinicians. Drug administration forms shall be determined by the dosage form of the pharmaceutical compound, suitable medicine forms are oral, parenteral injection, mucosal, muscular, intravenous, subcutaneous, intraocular, and intradermal or forms through the skin, etc. and the preferred choice is oral. In one of the specific implementations in this invention, the preferred dose is directly given through human trials. In another specific implementation, the preferred dose was given through animal (mice) experiments, and the dose for human can be calculated according to the equivalent dose relationship between human and test animals.

This invention quoted the publicly available literatures in order to describe this invention more clearly, and their full-text contents are incorporated herein as if their full text has been repeated in this article.

In order to make it understood easily, the following part will describe this invention with specific embodiments. It must be specially pointed out that these descriptions are only demonstrative and do not constitute a restriction on the scope of this invention. Other technical plans of this invention can be obtained by the method described in embodiments. According to the description of this instruction, many changes of this invention are obvious for technicians of its field.

Specific Implementation Methods

The plant raw materials and chemical reagents of specific embodiments are conventional materials which can be bought from the market.

Preparation of Experimental Medicines in Embodiment 1

(1) Preparation of Liquorices Extracts G007

Take 100 g *Glycyrrhiza uralensis* Fisch, crush it, and add 800 ml water to immerse it for bathing at 85° C. for seven hours. And then filter it to reserve the liquorices residue (solid), wash 3 times with warm water at 60° C., use 800 ml water each time, and soak the liquorices residue for 5 minutes, then filter it to remove water. Place the washed liquorices residue into an oven to dry it at 60° C. for seventeen hours, add 500 ml 95% (V/V) ethanol to the dried liquorices residue, reflow it in the water bath at 85° C. for 2.5 hours, then filter out the liquid for rotary evaporation and concentration, and place it into the oven at 60° C. for 20 hours to dry it, finally we can get 4.5 g liquorices extracts named G007

(2) Preparation of Liquorices Extracts ZG007

It is basically the same as the preparation of G007 take 100 g *Glycyrrhiza inflata* Batalin, crush it, add 800 ml water to immerse it for bathing at 85° C. for seven hours. And then filter it to reserve the liquorices residue (solid), wash 3 times with warm water at 60° C., use 800 ml water each time, and soak the liquorices residue for 5 minutes, then filter it to remove water. Place the washed liquorices residue into an oven to dry it at 60° C. for seventeen hours, add 500 ml 95% (V/V) ethanol to the dried liquorices residue, reflow it in the water bath at 85° C. for 2.5 hours, then filter out the liquid for rotary evaporation and concentration, and place it in the oven of 60 for 20 hours to dry it, finally we can get 5.3 g liquorices extracts named ZG007.

(3) Preparation of Chalcone A

Take the prepared ZG007 of the above step (2), 800 mg liquorices Chalcone A (99%) shall be separated from 7,000 mg ZG007 by high-speed countercurrent chromatography (HSCCC) according to the reported methods of Qiao-E. Wang, etc. (Journal of Chromatography A, 1048 (2004): 51-57), the solvent system is as follows: n-hexane-chloroform-methanol-water.

(4) Preparation of AG007-16

It can be made by the following steps: Dissolve 84 g prepared G007 of the above step (1) and 16 g prepared Chalcone A of the above step (3) in ethanol of 95% (V/V), after they are mixed evenly, dry it to remove the ethanol, then we can get it.

Calculate each component by HPLC, the percentage of the weight of indicator ingredients (total flavonoids, Chalcone A) contained in each extract of liquorices accounted is as shown in Table I:

TABLE I

The Content of Indicator Ingredients Contained in Each liquorices Extract

| Sample/components | The content of liquorices flavonoid + Chalcone A (%) | The content of Chalcone A (%) |
|---|---|---|
| G007 | 22.8 | Non-detected |
| ZG007 | 68.9 | 16 |
| AG007-16 | 35.2 | 16 |

(5) Preparation of A Wolfberry Powder

Crush 20 g raw wolfberry into powder, mix it with Chalcone A 100 mg got from the above step (3) or other sources evenly, and then we will get A wolfberry powder.

(6) Preparation of G007 Wolfberry Powder

Crush 20 g raw wolfberry into powder, mix it with G007 0.625 g got from the above step (1), and then we will get the G007 wolfberry powder.

(7) Other Medicines and Their Numbers

HBD09 is a kind of 99% chemically pure bis-indolymethane;

Cis-platinum (cisplantin), its purity is 99%;

I3C is a kind of 99% of chemically pure indole trismethanol.

The above medicines can be bought directly.

(8) Preparation of HBD09A 6 g HBD09 is obtained by mixing it evenly with Chalcone A got from the above step (3) or other sources.

Efficacy Studies of Various Drugs That Inhibit the Tumor Cells Growth in Embodiment 1 and Embodiment 2

Experiment Methods

1. Experimental Sources of In Vitro Killing Colon38 Cells

Colon38 cells i.e. murine colon carcinoma cells, which was gifted from Dept. of Pharmacology, Yale Medical School and are a kind of adherent cells.

Culture Medium:

90% 1640 culture solution plus 10% newborn calf serum (NCS), 100 ml in total, and then add 1ml miscible liquids containing 1% penicillin and 1% streptomycin.

Culture Conditions:

Cultivate it in an incubator of 37° C. with 5% CO2. The cells will passage every 3 days, and carry out the experiment when the cells enter their logarithmic growth period after two or three times of passage.

Experiment Procedures:

(1) Cultivate cells in logarithmic growth period; blow them into even distribution and prepare single cell suspension;

(2) Adjusting the cell concentration to 2×10/mL by RPMI1640 culture solution containing 10% FBS, inoculate them in a 96-hole cell cultivation board, 100 μL for each hole, cultivate it in an incubator of 37° C. with 5% CO2 for 24 hours;

(3) Dilute each drug in Embodiments 1 until the concentration reaches to: 1 μg/ml, 3 μg/ml, 9 μg/ml, 27 μg/ml, 81 μmg/ml.

(4) Add chemicals by group 24 hours later;

(5) Cultivate it for another 72 hours;

(6) We shall use the PBS plate washer, add 20 ul MTS solution and 100 ul RPMI1640 with 10% FBS into each hole, and cultivate it for 2 hours.
(7) We shall use the microplate reader A570 nm to compare the colors so as to determine the value of OD, compare the OD values of the dosing hole and comparison hole, calculate 50% inhibitory concentration (IC50) and/or 80% inhibitory concentration (IC80).

2. Experiment on In Vitro Killing of SGC-7901 Cell

Source:

SGC-7901 cells i.e. human gastric cancer cells which are bought from Cell Bank of Chinese Academy of Sciences/ Shanghai Institute of Life Sciences Cell Resource Center of Chinese Academy of Sciences are adherent cells.

Culture Medium:

90% 1640 culture solution plus 10% newborn calf serum (NCS), 100 ml in total, and then add 1ml miscible liquids containing 1% penicillin and 1% streptomycin.

Culture Conditions:

Cultivate it in an incubator of 37° C. with CO2 of 5 percent. The cells will passage once every 3 days, and carry out the experiment when the cells enter their logarithmic growth period after two or three times of passage.

Experiment Procedures:
(1) Cultivate cells in logarithmic growth period; blow them into even distribution and prepare single cell suspension;
(2) Adjusting the cell concentration to 2×10/mL by RPMI1640 medium containing 10% FBS, inoculate them in a 96-hole cell cultivation board, 100 μL for each hole, cultivate it in an incubator of 37° C. with 5% CO2 for 24 hours;
(3) Dilute each drug in Embodiments 1 until the concentration reaches to: 1 μg/ml, 3 μg/ml, 9 μg/ml, 27 μg/ml, 81 μg/ml.
(4) Add chemicals by group 24 hours later;
(5) Cultivate it for another 72 hours;
(6) We shall use the PBS plate washer, add 20 ul MTS solution and 100 ul RPMI1640 with 10% FBS into each hole, and cultivate it for 2 hours.
(7) We shall use the microplate reader A570 nm to compare the colors so as to determine the value of OD, compare the OD values of the dosing hole and comparison hole, calculate 50% inhibitory concentration (IC50) and/or 80% inhibitory concentration (IC80).

3. Experiment on In Vitro Killing of MCF-7 Cell

Source

MCF-7 cells i.e. human breast cancer cells, which are bought from American ATCC, is a kind of adherent cells.

Culture Medium:

90% 1640 medium+10% fetal calf serum+30mmol/L Hepes+6 μg/ml insulin.

Its culture conditions and experimental procedures are all the same with that of the above method 1.

4. Experiment on In Vitro Killing of PC-3 Cell

Source

PC-3 cells i.e. prostate cancer cells, which are bought from American ATCC, is a kind of adherent cells.

Its medium, culture conditions and experimental procedures are all the same with that of the above method 1.

II. Experiment Results

Results from the study are as shown in Table II, all liquorices extracts perform well in inhibiting tumor cells, although not that powerful as Cis-platinum, they are all more effective than I3C.

TABLE II

Effects of Liquorices Extracts on Inhibiting Tumor Cells

| Experiment cell | Results | G007 | ZG007 | Chalcone A | AG007-16 | Cis-platinum | HBD09 | I3C |
|---|---|---|---|---|---|---|---|---|
| Colon38 | IC50 (μg/ml) | 18.6 | 17.3 | 9.1 | 13.31 | 3.92 | 18.59 | 76.3 |
|  | IC80 (μg/ml) | 50.21 |  | 24.77 |  |  | 48.51 |  |
| SGC-7901 | IC50 (μg/ml) | 24.0 | 19.5 | 9.7 | 21.7 | 5.4 | 18.2 | 63.5 |
|  | IC80 (μg/ml) | 47.78 |  | 29.70 |  |  | 51.24 |  |
| MCF-7 | IC50 (μg/ml) | 17.6 | 17.3 | 9.1 | 13.31 | 3.92 | 15.6 | 89.8 |
|  | IC80 (μg/ml) | 35.6 |  | 21.3 |  |  | 31.2 |  |
| PC-3 | IC50 (μg/ml) | 19.6 | 19.9 | 7.8 | 12.31 | 3.52 | 13.8 | 56.4 |
|  | IC80 (μg/ml) | 34.4 |  | 13.3 |  |  | 23.9 |  |

Study on Efficacy of the Combination of all Drugs in Embodiment 3 and Embodiment 1 in Inhibiting the Growth of Tumor Cells Synergistic effects of the combination of two drugs are represented by Combination Index (CI) value calculated with the formula issued by Chou and Talalay (Chou T C, Talalay P. Adv.Enzyme regul. 1984; 22:27-55). CI<1 shows synergism from mutual combination, CI=1 shows simple compound of effects, and CI>1 shows impairment of effects from mutual counter-interaction.

According to the cells and experiment methods used in Embodiment 2, differences are incurred from that dose concentration is confirmed by the following methods: when two drugs are combined, the concentration of one drug is chosen to be approximate to but smaller than IC50 while the concentration of other drugs is chosen to be in gradient dilution, to perform a series of experiments. When it is experimented that 50% tumor cells are inhibited, then the concentration of all drugs used at that moment is recorded as their IC50 value, and the CI value of the two drugs can be calculated with the formula in the above document.

The results are shown in Table III, Chalcone A makes synergistic effects on Liquorices flavonoid extracts G007containing without Chalcone A, I3C and its derivatives DIM. AG007-16 or ZG007-16 has synergistic effects on I3C and its derivatives DIM. Surprisingly, Liquorices flavonoid extracts ZAG198 containing without Chalcone A also has synergistic effects on I3C and its derivatives DIM and the commonly used anti-cancer drug Cis-platinum.

This shows that Chalcone A and liquorices extracts (such as G007, ZG007) containing or not containing Chalcone A all have synergistic effects on I3C and its derivatives DIM, and anti-cancer drugs such as Cis-platinum etc. In addition, Chalcone A combined with liquorices extracts G007 containing without Chalcone A can also produces synergistic effects, which shows that it is more preferred to obtain liquorices extracts by extracting liquorices containing Chalcone A and not containing Chalcone A in a mixed way or by extracting different liquorices extracts containing Chalcone A and not containing Chalcone A and then to mix it.

TABLE III

Effects of drug combination on inhibiting tumor cells

| Drug | Cell Colon 38 IC 50 (μg/ml) | | CI |
|---|---|---|---|
| Chalcone A + G007 | 2.1 (Chalcone A) | 11.0 (G007) | 0.86 |
| Chalcone A + HBD09 | 1.97 (Chalcone A) | 9 (HBD09) | 0.68 |
| Chalcone A + I3C | 5.7 (Chalcone A) | 9 (I3C) | 0.74 |
| AG007-16 + HBD09 | 5.6 (AG007-16) | 9 (HBD09) | 0.88 |
| HBD09 + G007 | 9 (HBD09) | 7.57 (G007) | 0.89 |
| I3C + G007 | 6.8 (I3C) | 9 (G007) | 0.78 |
| G007 + Cis-platinum | 9 (G007) | 1.1 (Cis-platinum) | 0.77 |

TABLE III-continued

Effects of drug combination on inhibiting tumor cells

| Drug | Cell SGC-7901 IC 50 (μg/ml) | | CI |
|---|---|---|---|
| Chalcone A + HBD09 | 1.82 (Chalcone A) | 9 (HBD09) | 0.73 |
| G007 + HBD09 | 5.15 (G007) | 9 (HBD09) | 0.57 |
| G007 + Cis-platinum | 9 (G007) | 2.6 (Cis-platinum) | 0.63 |

Clinical Observation on the Efficacy of all Drugs in Embodiment 4 and Embodiment 1 on Postprandial Blood Glucose Controlling for High-Blood-Glucose Patient The postprandial blood glucose of Type 2 diabetics not sensitive to insulin is an important index of abnormal glucose metabolism and can be used to test the effect of drugs in reducing blood glucose. Implemented according to the clinical experiment standard of State Food and Drug Administration, people of different groups (45-56 years old, three in one group, fasting blood glucose is above 7.5 mM/L and postprandial blood glucose is above 10 mM/L) take orally Chalcone A, G007, AG007-16, A wolfberry powder, G007 wolfberry powder, wolfberry powder, and soybean powder (as negative control) prepared in Embodiment 1, and the dose they intake before meal is respectively 56 mg, 350 mg, 350 mg, 15 g, 15 g, 15 g and 15 g. Test the blood glucose two hours after the patients eat 300 g boiled corn, and the results are as shown in Table IV.

The results show that Chalcone A, G007, AG007-16, A wolfberry powder, G007 wolfberry powder and wolfberry powder all have significant effects on controlling postprandial blood glucose of high-blood-glucose patients and perform greatly better than ordinary foods (soybean), among which, combination drugs such as A wolfberry powder and G007 wolfberry powder etc work best.

TABLE IV

Blood Glucose Comparison before/after Meal with/without Drug Intake

| Drug | Patient No. | Gender | Age | Without drug intake, before/after meal | | Drug intake, before/after meal | |
|---|---|---|---|---|---|---|---|
| | | | | Blood glucose (mM/L) | Blood glucose (mM/L) | Blood glucose (mM/L) | Blood glucose (mM/L) |
| Chalcone A | 10-1 | F | 59 | 8.3 | 12.8 | 8.5 | 11.6 |
| | 10-2 | F | 54 | 7.8 | 13.9 | 7.9 | 10.6 |
| | 10-3 | F | 46 | 8.6 | 12.9 | 8.6 | 12.0 |
| | Average ratio of glucose reduction | | | | 13.2 | | 11.4 13.6% |
| G007 | 10-4 | M | 55 | 9.0 | 13.4 | 9.3 | 8.5 |
| | 10-5 | M | 51 | 8.1 | 13.5 | 8.2 | 9.8 |
| | 10-6 | M | 50 | 7.8 | 14.3 | 7.9 | 8.7 |
| | Average ratio of glucose reduction | | | | 13.7 | | 9.0 34% |
| AG007-16 | 10-7 | F | 60 | 6.8 | 11.8 | 6.8 | 7.9 |
| | 10-8 | F | 65 | 7.5 | 12.3 | 7.5 | 7.5 |
| | 10-9 | F | 60 | 6.8 | 12.6 | 6.8 | 7.1 |
| | Average ratio of glucose reduction | | | | 12.2 | | 7.5 39% |
| A wolfberry powder | 10-10 | F | 65 | 7.6 | 12.3 | 7.5 | 6.5 |
| | 10-11 | M | 59 | 8.4 | 13.2 | 8.4 | 6.8 |
| | 10-12 | F | 65 | 8.3 | 12.3 | 8.1 | 7.3 |
| | Average ratio of glucose reduction | | | | 12.6 | | 6.9 45% |

TABLE IV-continued

Blood Glucose Comparison before/after Meal with/without Drug Intake

|  |  |  |  | Without drug intake, before/after meal | | Drug intake, before/after meal | |
| --- | --- | --- | --- | --- | --- | --- | --- |
| Drug | Patient No. | Gender | Age | Blood glucose (mM/L) | Blood glucose (mM/L) | Blood glucose (mM/L) | Blood glucose (mM/L) |
| G007 wolfberry powder | 10-10 | F | 65 | 7.5 | 11.9 | 7.3 | 6.1 |
|  | 10-11 | M | 59 | 8.2 | 13.5 | 8.4 | 5.2 |
|  | 10-12 | F | 65 | 7.8 | 11.8 | 7.5 | 6.8 |
|  | Average ratio of glucose reduction |  |  |  | 12.4 |  | 6.0 52% |
| Wolfberry powder | 10-10 | F | 65 | 7.7 | 13.8 | 7.5 | 8.0 |
|  | 10-11 | M | 59 | 8.2 | 12.5 | 8.1 | 8.5 |
|  | 10-12 | F | 65 | 7.9 | 11.8 | 8.0 | 8.9 |
|  | Average ratio of glucose reduction |  |  |  | 12.7 |  | 8.5 33% |
| Soybean powder | 10-10 | F | 65 | 7.8 | 12.5 | 7.5 | 11.6 |
|  | 10-11 | M | 59 | 8.4 | 11.9 | 8.3 | 10.8 |
|  | 10-12 | F | 65 | 8.1 | 12.5 | 8.5 | 12.6 |
|  | Average ratio of glucose reduction |  |  |  | 12.3 |  | 11.7 5% |

Clinical Observation on the Efficacy of all Drugs in Embodiment 5 and Embodiment 1 for High-Blood-Glucose and High Blood Lipid (i.e. "Two Highs") Patients Implemented according to the clinical experiment standard of State Food and Drug Administration, people of different groups (45-56 years old, ten in one group, men and women take up half respectively, fasting blood glucose is above 7.5 mM/L and the serum cholesterol is above 300 mg/100 ml) take orally wolfberry powder, A wolfberry powder, and G007 wolfberry powder, and each 15 g, take each time before breakfast every day, four weeks in total. Test the blood glucose and blood lipid four weeks later, and the results are as shown in Table V.

The results show that the average blood glucose reduced by the combination drug of A wolfberry powder and G007 wolfberry powder for "Two Highs" patients is about 30%, and the average serum cholesterol is reduced by about 45%, which is much better than the compared effect of wolfberry on reducing blood glucose by less than 15% and blood lipid less than 5%.

TABLE V

Fasting Blood Glucose and Lipid Comparison before and after Drug Intake

|  |  |  |  | Before drug use | | After drug use | |
| --- | --- | --- | --- | --- | --- | --- | --- |
| Drug | Patient No. | Gender | Age | Blood glucose (mM/L) | Cholesterol (mg/100 ml) | Blood glucose (mM/L) | Cholesterol (mg/100 ml) |
| Wolfberry powder | 05-11 | M | 51 | 8.7 | 320 | 7.8 | 309 |
|  | 05-12 | M | 51 | 7.6 | 319 | 6.9 | 320 |
|  | 05-13 | M | 53 | 8.9 | 352 | 7.8 | 343 |
|  | Average ratio of reduction |  |  | 8.4 | 330 | 7.5 11% | 324 1.8% |
| A wolfberry powder | 06-14 | F | 47 | 8.2 | 335 | 5.6 | 209 |
|  | 07-15 | F | 50 | 8.5 | 351 | 6.3 | 211 |
|  | 07-16 | F | 48 | 9.6 | 436 | 6.5 | 203 |
|  | Average ratio of reduction |  |  | 8.8 | 374 | 6.1 31% | 207 45% |
| G007 wolfberry powder | 07-17 | F | 61 | 8.9 | 298 | 5.8 | 198 |
|  | 07-18 | M | 65 | 8.6 | 355 | 6.5 | 201 |
|  | 07-19 | F | 56 | 8.3 | 438 | 6.1 | 186 |
|  | Average ratio of reduction |  |  | 8.6 | 364 | 6.1 30% | 194 47% |

Embodiment 6 Anti-Tumor Effects From Combination of Drug Compositions With Chemotherapy Drugs on Animal Models Based on the method described in *Pharmacology Research Methodology of Chinese Medicine* (Chinese TCM Publishing House), test the anti-tumor effects of Chalcone A, G007, AG007-16 etc prepared in Embodiment 1, chemotherapy drugs (5-fluorouracil) and HBD09 on animal model of human cancer heterogeneity transplanted tumor. 5-fluorouracil (short for fu) is a broad-spectrum anti-tumor drug and mainly used to cure digestive tract tumor; the common adverse reactions are sicchasia, anorexia or vomiting, abdominal discomfort or diarrhea.

To be short, the test method is to inoculate human colon cancer cell strain colon38 to the subcutaneous part of mice weighing at 18-23 g, and 14 days after inoculation, give dose of Chalcone A, G007, AG007-16, ZG007-16, HBD09, A wolfberry powder etc prepared in Embodiment 1 to each group of animals separately by respective intragastric administration, or 0.5-1 hour after intragastric administration, inject intra-peritoneally with chemotherapy drugs such as 5-fluorouracil (fu) etc; normal saline is given to negative control group (CK) and fu is given to positive control group (CK1). The dose given is as shown in Table VI; intragastric administration/ or injection administration is given once a week and four times in total. The results after four weeks are as shown in Table VI, in which, the number of dead animals (death number) represents the side effects caused by drugs.

The results show that, though Chalcone A, G007 and AG007-16 etc performs poorer than 5-fluorouracil, when they are used in combination with 5-fluorouracil, liquorices extracts such as Chalcone A, G007 and AG007-16 etc all can reduce the side effects brought by 5-fluorouracil dose. Besides, liquorices extracts like Chalcone A, G007 and AG007-16 etc also have synergistic effects to enhance the function to inhibit tumor. More surprisingly, A wolfberry powder, a curing preparation that can be taken as food or health care products, performs pretty well in inhibiting tumor.

TABLE VI

Effects on Inhibiting Tumor Growth

| Group | Drug dose | Average weight of tumor (g) | Tumor inhibiting rate (%)* | Death number | Experiment number in total |
|---|---|---|---|---|---|
| CK | Non (Controlling group) | 3.06 ± 0.16 | — | 0 | 10 |
| CK1(fu) | 30 mg/kg | 1.74 ± 0.11 | 43% | 6 | 10 |
| Chalcone A | 100 mg/kg | 2.36 ± 0.13 | 23% | 0 | 10 |
| HBD09 | 600 mg/kg | 2.6 ± 0.15 | 15% | 2 | 10 |
| Chalcone A + fu | 100 mg/kg + 20 mg/kg | 0.99 ± 0.13 | 68% | 1 | 10 |
| Chalcone A + HBD09 | 100 mg/kg + 600 mg/kg | 1.35 ± 0.11 | 56% | 0 | 10 |
| G007 + fu | 350 mg/kg + 20 mg/kg | 0.92 ± 0.12 | 70% | 0 | 10 |
| AG007-16 + fu | 350 mg/kg + 20 mg/kg | 0.83 ± 0.15 | 73% | 0 | 10 |
| ZG007-16 + fu | 350 mg/kg + 20 mg/kg | 0.95 ± 0.13 | 69% | 1 | 10 |
| A wolfberry powder | 3 g/kg | 0.77 ± 0.11 | 75% | 0 | 10 |

*Tumor inhibiting rate (%) = (Average tumor weight of CK Group − Average tumor weight of Experiment Group)/CK average tumor weight × 100% (4)

The invention claimed is:

1. A drug composition, comprising alcohol-soluble and water-insoluble liquorice extract, and at least one anti-tumor or glucose-or/and-lipid-lowering drug/eatable substance, wherein the anti-tumor or glucose-or/and-lipid-lowering drug/eatable substance is selected from the group consisting of 5-fluorouracil, bis-indolymethane, Cis-platinum, wolfberry and mixtures thereof, and wherein the anti-tumor or glucose-or/and-lipid-lowering drug/eatable substance and the liquorice extract are present in amounts sufficient to produce a combination index (CI) of <1.

2. The drug composition of claim 1, wherein the liquorice extract comprises extract of radix glycyrrhiza including Glycyrrhiza uralensis or glycyrrhiza inflata or a mixture thereof.

3. The drug composition of claim 1, wherein the alcohol-soluble and water-insoluble liquorice extract is prepared through a method including the following steps:
   (1) Reserve solid parts after extraction of liquorice by water;
   (2) Reserve and dry remaining liquid part, after extracting the solid parts in step (1), with a high concentration alcohol having a concentration higher than 85% (V/V).

4. The drug composition of claim 3, wherein the method further includes the step to extract Chalcone A.

5. The drug composition of claim 1, wherein the liquorice extract contains liquorice flavonoid in an amount higher than 15%.

6. An anti-tumor or blood-glucose-and lipid-reduction pharmaceutical drug comprising the drug composition of claim 1 and a pharmaceutically acceptable adjuvant, and wherein the liquorice extract is present in amounts which are safe and effective.

7. The drug composition of claim 1, wherein the at least one anti-tumor or glucose-or/and-lipid-lowering drug/eatable substance is anti-tumor or glucose-and-lipid-lowering drug/eatable substance.

8. The drug composition of claim 2, wherein the liquorice extract is a mixture of Glycyrrhiza uralensis and glycyrrhiza inflata.

9. The drug composition of claim 8, wherein the mixture contains more than 5% by weight of glycyrrhiza inflata.

10. The drug composition of claim 3, wherein the high concentration alcohol has a concentration higher than 90% (v/v).

11. The drug composition of claim 3, wherein the high concentration alcohol has a concentration higher than 93% (v/v).

12. The drug composition of claim 3, wherein the high concentration alcohol has a concentration higher than 95% (v/v).

13. The drug composition described in claim 1, wherein the anti-tumor or glucose-or/and-lipid-lowering drug/eatable substance is at least one chemotherapy agent for anti-cancer application.

14. The drug composition of claim 4, wherein the composition contains Chalcone A in an amount higher than 5% by weight.

* * * * *